US011112375B2

(12) United States Patent
Chen et al.

(10) Patent No.: US 11,112,375 B2
(45) Date of Patent: Sep. 7, 2021

(54) NANOPORE-BASED SEQUENCING WITH VARYING VOLTAGE STIMULUS

(71) Applicant: Roche Sequencing Solutions, Inc., Pleasanton, CA (US)

(72) Inventors: Roger J. A. Chen, Saratoga, CA (US); J. William Maney, Jr., Emerald Hills, CA (US); Hui Tian, Cupertino, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 16/719,774

(22) Filed: Dec. 18, 2019

(65) Prior Publication Data

US 2020/0124559 A1 Apr. 23, 2020

Related U.S. Application Data

(63) Continuation of application No. 15/820,032, filed on Nov. 21, 2017, now Pat. No. 10,545,112, which is a continuation of application No. 14/971,667, filed on Dec. 16, 2015, now Pat. No. 9,863,904, which is a
(Continued)

(51) Int. Cl.
*G01N 27/22* (2006.01)
*C12Q 1/6869* (2018.01)
*G01N 27/447* (2006.01)
*G01N 33/487* (2006.01)

(52) U.S. Cl.
CPC ......... *G01N 27/228* (2013.01); *C12Q 1/6869* (2013.01); *G01N 27/44791* (2013.01); *G01N 33/48721* (2013.01)

(58) Field of Classification Search
CPC ... G01N 27/228; G01N 27/447–44795; G01N 27/48721; G01N 27/48728; B01D 57/00–02
USPC ................ 204/450–470, 546–550, 600–621, 204/643–645
See application file for complete search history.

(56) References Cited

U.S. PATENT DOCUMENTS

2011/0226623 A1* 9/2011 Timp .................. C12Q 1/6869
204/543
2013/0341192 A1 12/2013 Dunbar et al.

FOREIGN PATENT DOCUMENTS

| CN | 103154265 A | 6/2013 |
| CN | 103328972 A | 9/2013 |
| CN | 105612260 A | 5/2016 |

(Continued)

*Primary Examiner* — Bach T Dinh
(74) *Attorney, Agent, or Firm* — Roche Sequencing Solutions, Inc.

(57) ABSTRACT

A method of analyzing a molecule is disclosed. A voltage source is selectively connected to or disconnected from a capacitor using a switch controlled by a reset signal. A charge is stored in a capacitor when the voltage source is connected to the capacitor. The capacitor is discharged through a nanopore in a membrane when the voltage source is disconnected from the capacitor. A duty cycle of the reset signal is determined such that the voltage source and the capacitor is connected for at least a one tenth portion of a reset signal period and disconnected for a remaining portion of the reset signal period, such that a voltage across the nanopore is maintained at a higher level during the portion of the reset signal period in which the connection is maintained than during the remaining portion of the reset signal period in which the connection is not maintained.

13 Claims, 14 Drawing Sheets

Related U.S. Application Data continuation-in-part of application No. 14/577,511, filed on Dec. 19, 2014, now Pat. No. 9,557,294.

(56) References Cited

FOREIGN PATENT DOCUMENTS

| | | | |
|---|---|---|---|
| WO | 2011143340 | A2 | 11/2011 |
| WO | 2013130635 | A2 | 9/2013 |
| WO | WO2013/155116 | * | 10/2013 |
| WO | 2013130635 | A3 | 11/2014 |
| WO | 2015057324 | A2 | 4/2015 |

* cited by examiner

NANOPORE-BASED SEQUENCING WITH VARYING VOLTAGE STIMULUS

CROSS REFERENCE TO OTHER APPLICATIONS

This application is a continuation of U.S. patent application Ser. No. 15/820,032, entitled NANOPORE-BASED SEQUENCING WITH VARYING VOLTAGE STIMULUS, filed Nov. 21, 2017, which is a continuation of U.S. patent application Ser. No. 14/971,667, now U.S. Pat. No. 9,863,904, entitled NANOPORE-BASED SEQUENCING WITH VARYING VOLTAGE STIMULUS, filed Dec. 16, 2015, which is a continuation in part of U.S. patent application Ser. No. 14/577,511, now U.S. Pat. No. 9,557,294, entitled NANOPORE-BASED SEQUENCING WITH VARYING VOLTAGE STIMULUS, filed Dec. 19, 2014, each of which are incorporated herein by reference for all purposes.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

FIG. 10 illustrates an embodiment of the plots of the voltage applied across the nanopore versus time when the nanopore is in different states.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
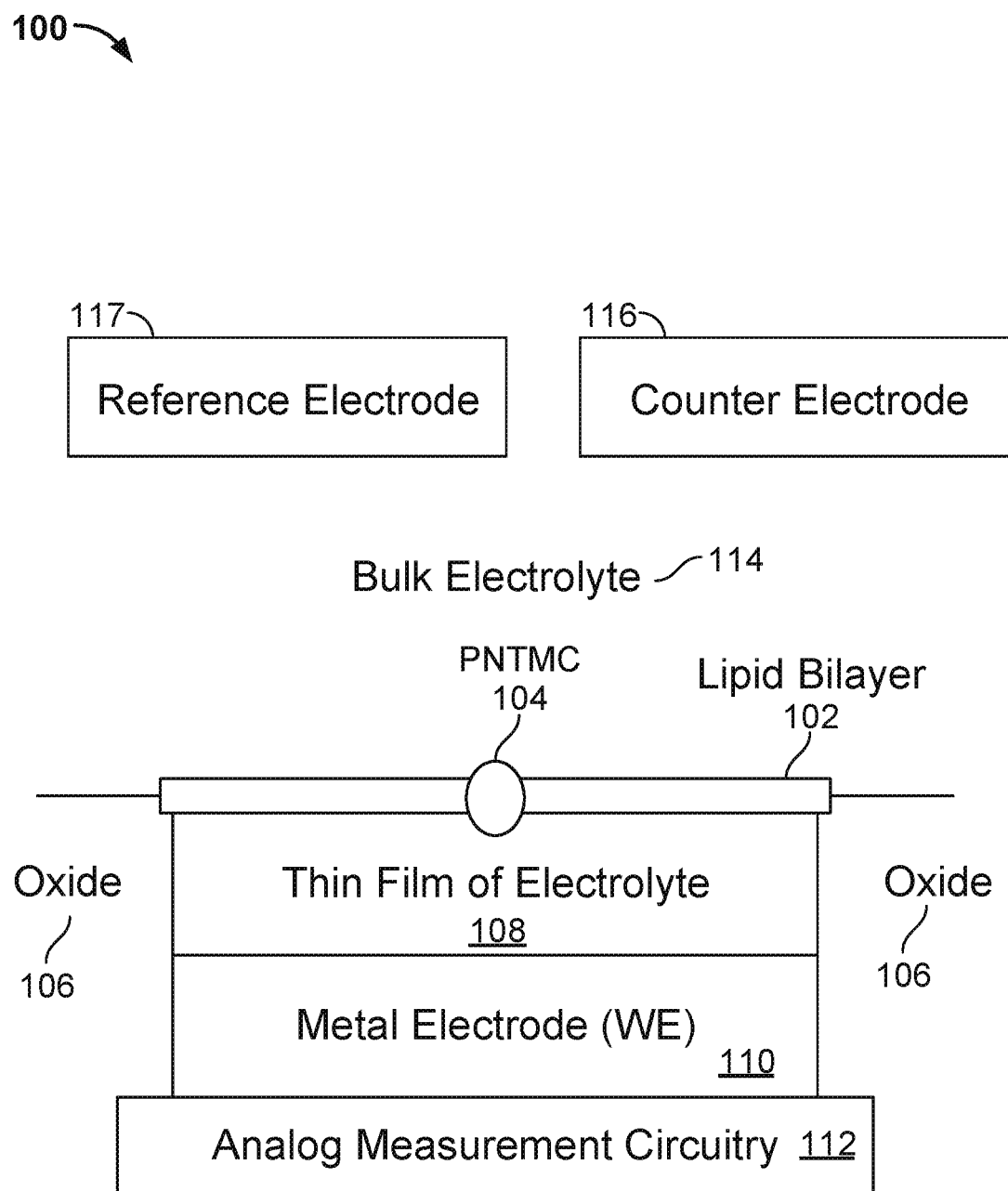
FIG. 1 illustrates an embodiment of a cell 100 in a nanopore based sequencing chip.

FIG. 1 illustrates an embodiment of a cell 100 in a nanopore based sequencing chip. A membrane 102 is formed over the surface of the cell. In some embodiments, membrane 102 is a lipid bilayer. The bulk electrolyte 114 containing soluble protein nanopore transmembrane molecular complexes (PNTMC) and the analyte of interest is placed directly onto the surface of the cell. A single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is an electrochemical potential sensor. The cell also includes a reference electrode 117.

Figure 2:
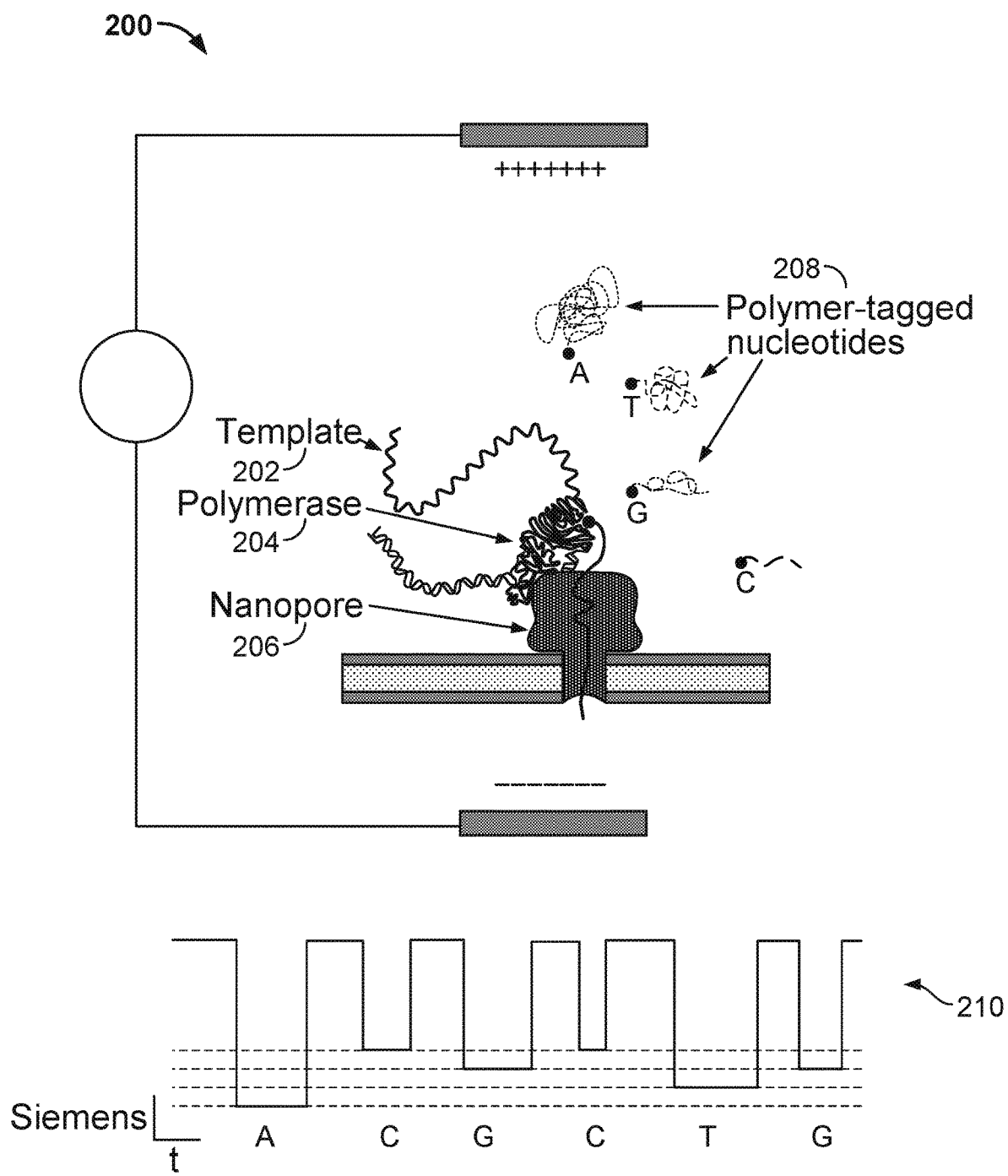
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
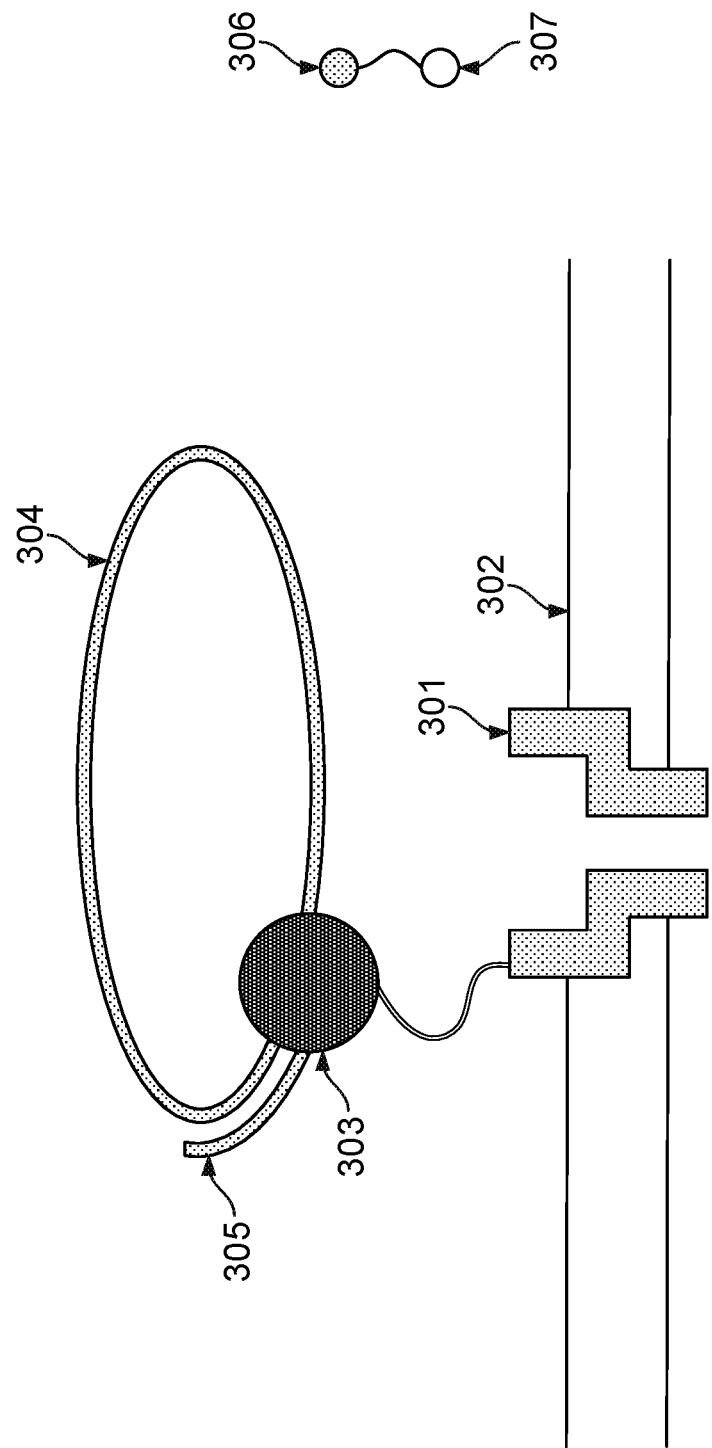
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
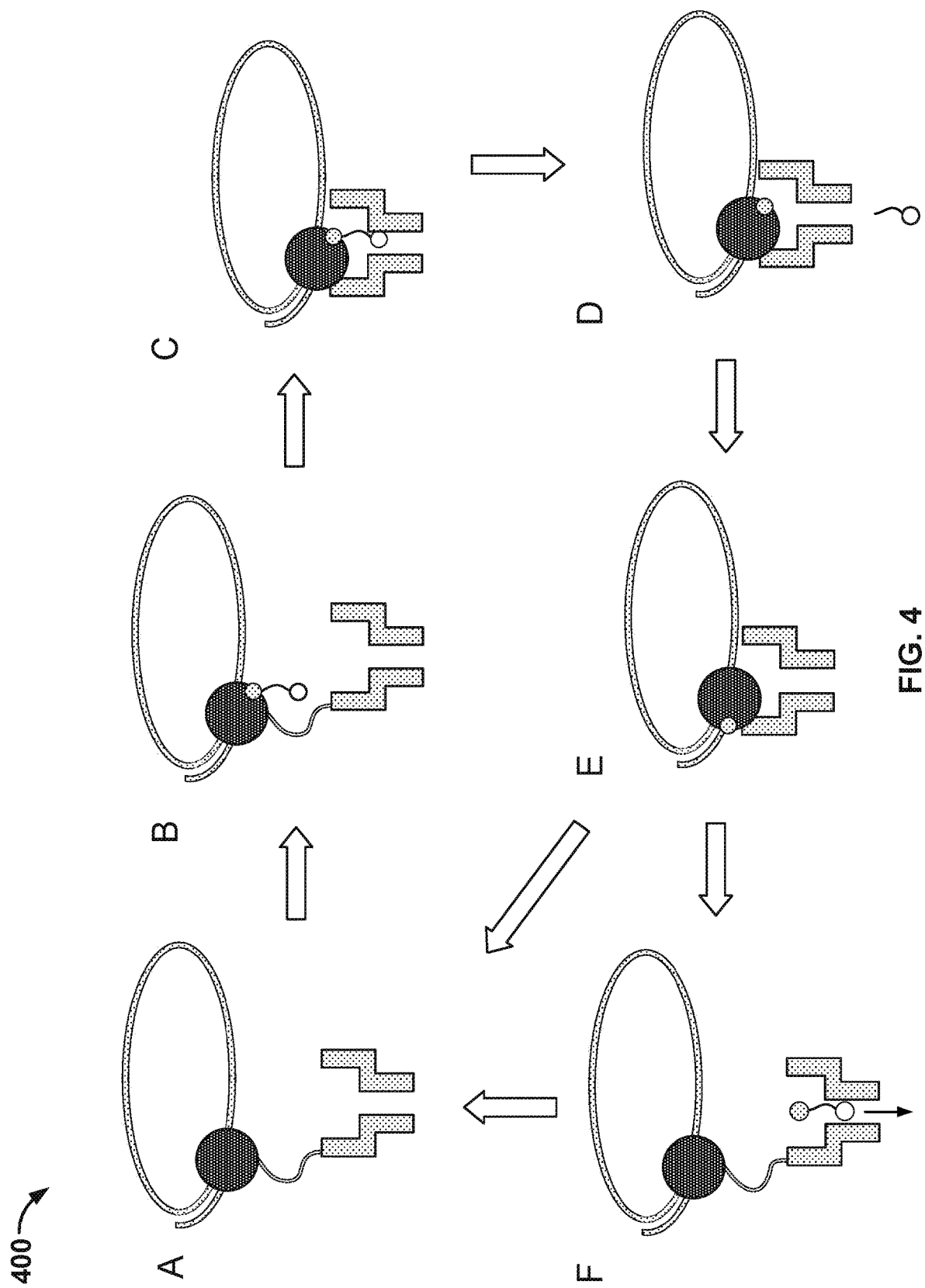
FIG. 4 illustrates an embodiment of a process 400 for nucleic acid sequencing with pre-loaded tags.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 10000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the conductance of the nanopore is ~300 picosiemens (300 pS). At stage C, the conductance of the nanopore is about 60 pS, 80 pS, 100 pS, or 120 pS, corresponding to one of the four types of tagged nucleotides respectively. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
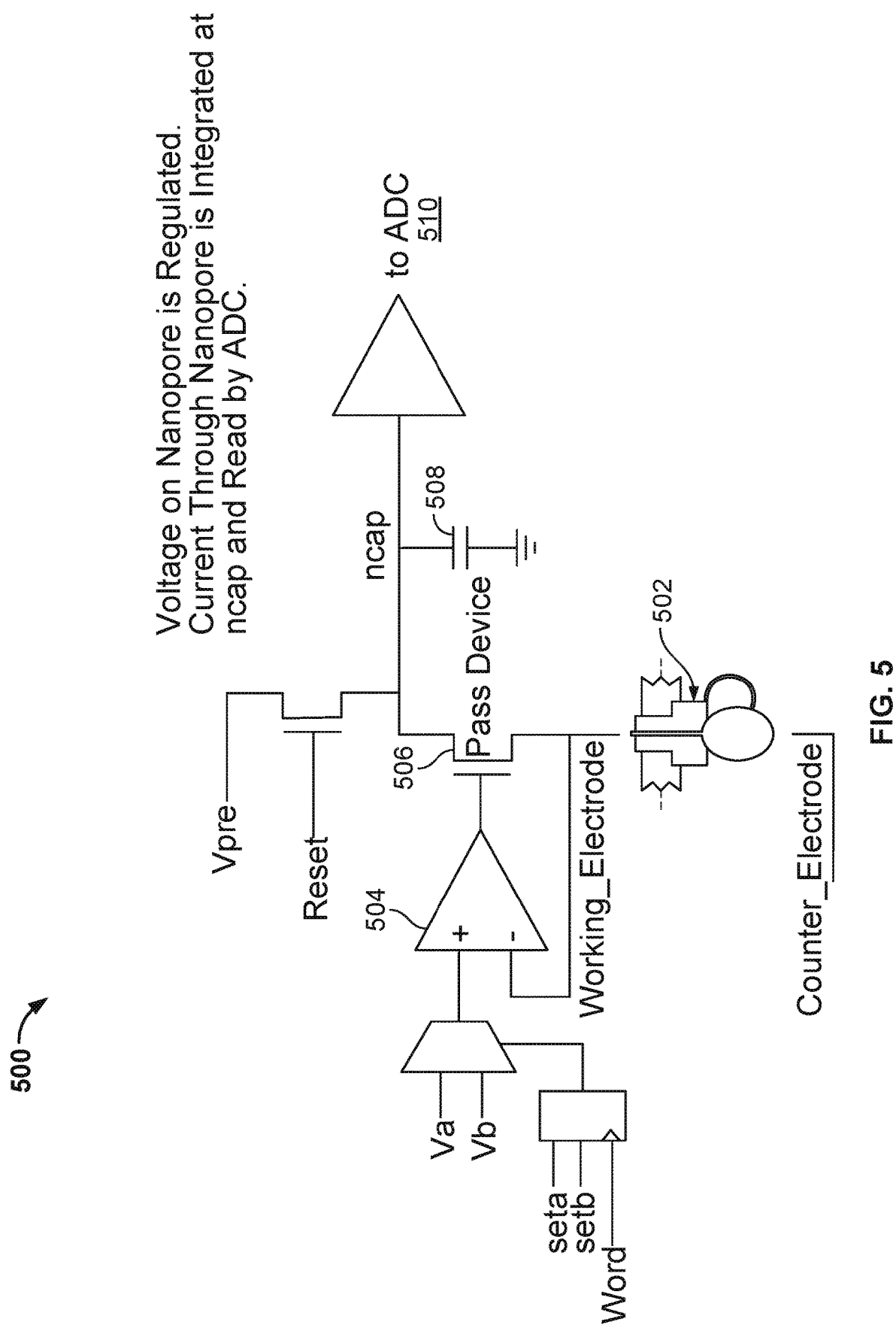
FIG. 5 illustrates an embodiment of a circuitry 500 in a cell of a nanopore based sequencing chip.

FIG. 5 illustrates an embodiment of a circuitry 500 in a cell of a nanopore based sequencing chip. As mentioned above, when the tag is held in nanopore 502, a unique conductance signal (e.g., see signal 210 in FIG. 2) is generated due to the tag's distinct chemical structures, thereby identifying the added base electronically. The circuitry in FIG. 5 maintains a constant voltage across nanopore 502 when the current flow is measured. In particular, the circuitry includes an operational amplifier 504 and a pass device 506 that maintain a constant voltage equal to $V_a$ or $V_b$ across nanopore 502. The current flowing through nanopore 502 is integrated at a capacitor $n_{cap}$ 508 and measured by an Analog-to-Digital (ADC) converter 510.

However, circuitry 500 has a number of drawbacks. One of the drawbacks is that circuitry 500 only measures unidirectional current flow. Another drawback is that operational amplifier 504 in circuitry 500 may introduce a number of performance issues. For example, the offset voltage and the temperature drift of operational amplifier 504 may cause the actual voltage applied across nanopore 502 to vary across different cells. The actual voltage applied across nanopore 502 may drift by tens of millivolts above or below the desired value, thereby causing significant measurement inaccuracies. In addition, the operational amplifier noise may cause additional detection errors. Another drawback is that the portions of the circuitry for maintaining a constant voltage across the nanopore while current flow measurements are made are area-intensive. For example, operational amplifier 504 occupies significantly more space in a cell than other components. As the nanopore based sequencing chip is scaled to include more and more cells, the area occupied by the operational amplifiers may increase to an unattainable size. Unfortunately, shrinking the operational amplifier's size in a nanopore based sequencing chip with a large-sized array may raise other performance issues; for example, it may exacerbate the offset and noise problems in the cells even further.

Figure 6:
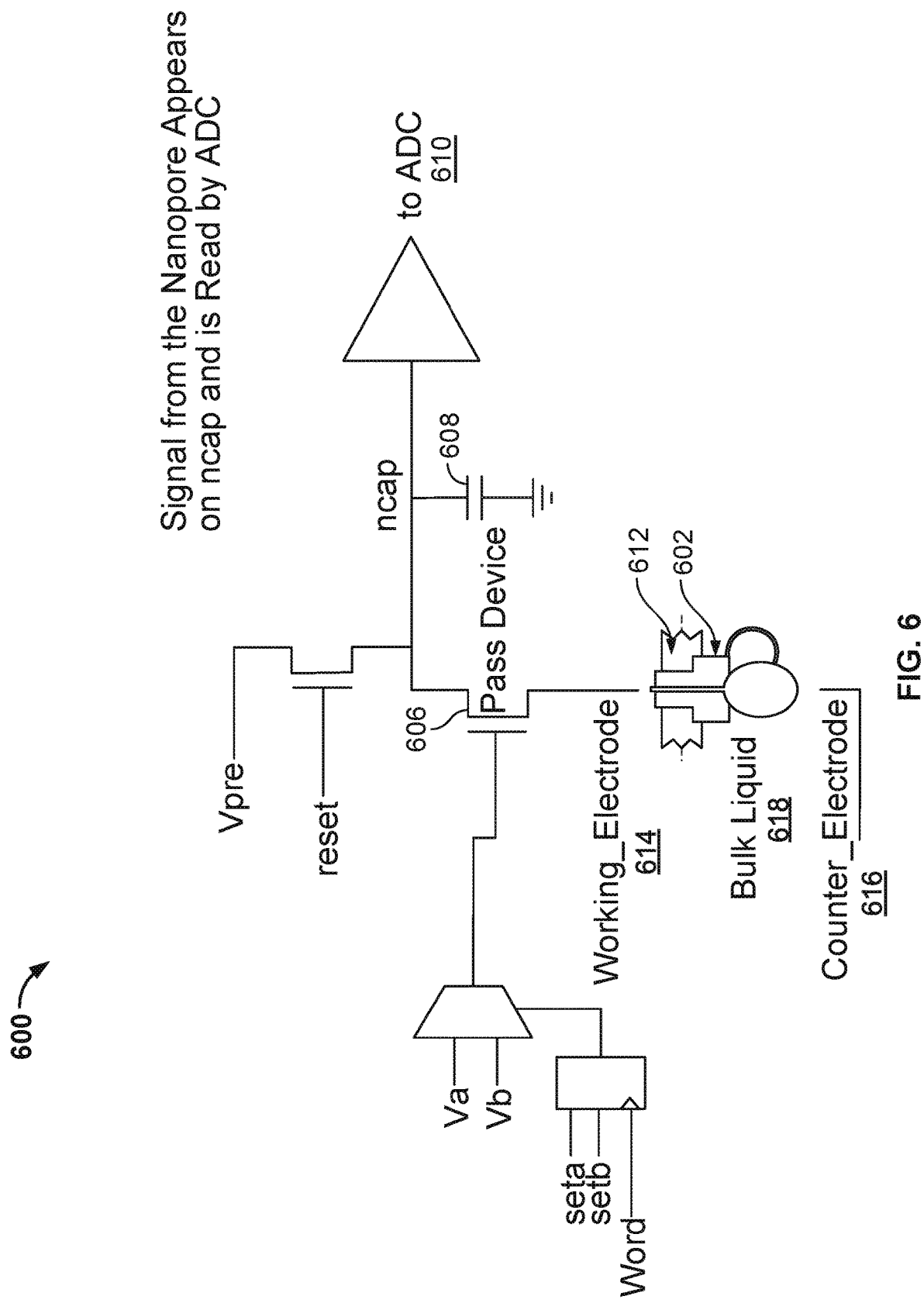
FIG. 6 illustrates an embodiment of a circuitry 600 in a cell of a nanopore based sequencing chip, wherein the voltage applied across the nanopore can be configured to vary over a time period during which the nanopore is in a particular detectable state.
Figure 7A:
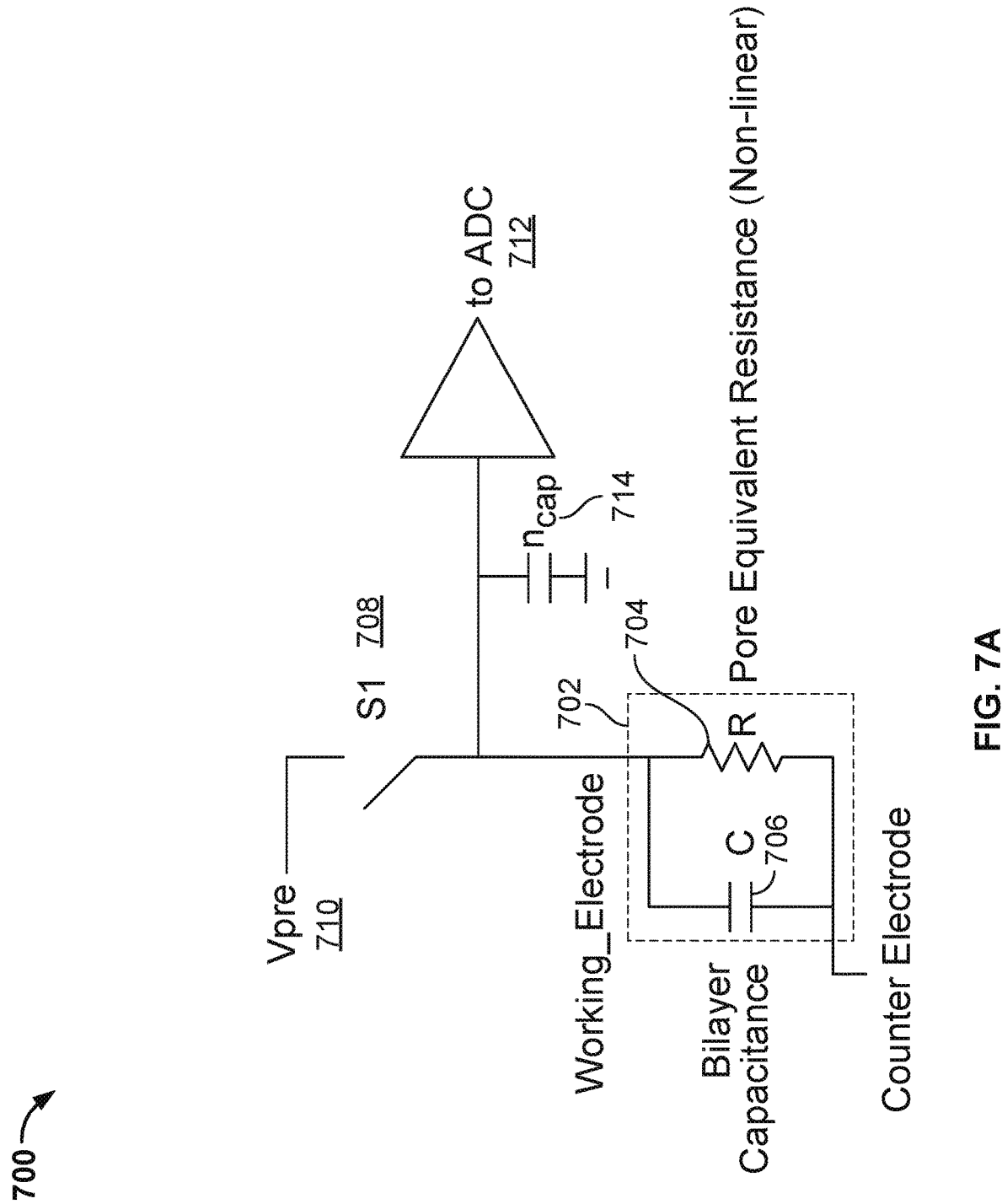
FIG. 7A illustrates an additional embodiment of a circuitry 700 in a cell of a nanopore based sequencing chip, wherein the voltage applied across the nanopore can be configured to vary over a time period during which the nanopore is in a particular detectable state.
Figure 7B:
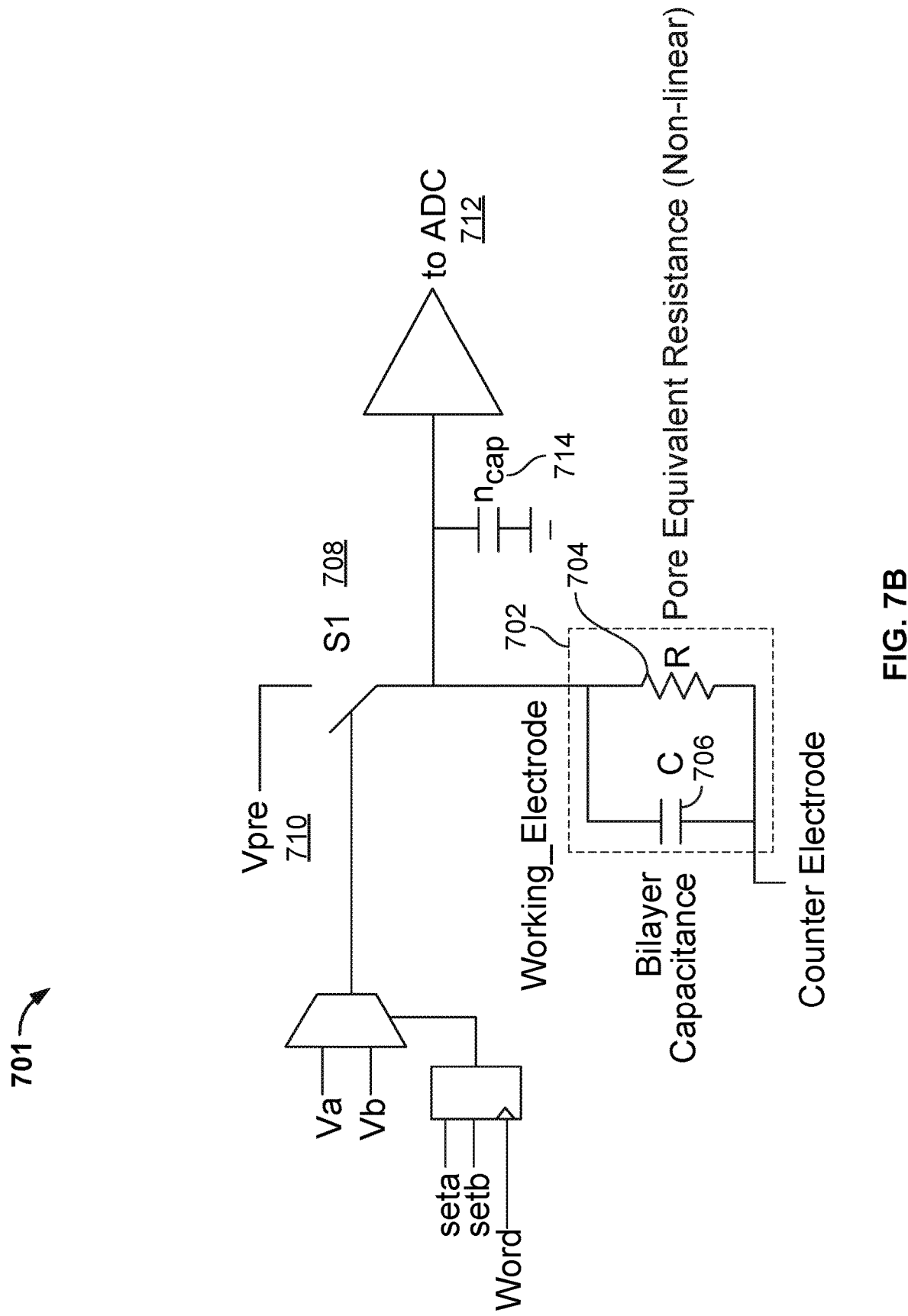
FIG. 7B illustrates an additional embodiment of a circuitry 701 in a cell of a nanopore based sequencing chip, wherein the voltage applied across the nanopore can be configured to vary over a time period during which the nanopore is in a particular detectable state.

FIG. 6 illustrates an embodiment of a circuitry 600 in a cell of a nanopore based sequencing chip, wherein the voltage applied across the nanopore can be configured to vary over a time period during which the nanopore is in a particular detectable state. One of the possible states of the nanopore is an open-channel state, in which a tag-attached polyphosphate is absent from the barrel of the nanopore. Another four possible states of the nanopore correspond to the states when the four different types of tag-attached polyphosphate (A, T, G, or C) are held in the barrel of the nanopore. Yet another possible state of the nanopore is when the membrane is ruptured. FIGS. 7A and 7B illustrate additional embodiments of a circuitry (700 and 701) in a cell of a nanopore based sequencing chip, wherein the voltage applied across the nanopore can be configured to vary over a time period during which the nanopore is in a particular detectable state. In the above circuits, the operational amplifier is no longer required.

FIG. 6 shows a nanopore 602 that is inserted into a membrane 612, and nanopore 602 and membrane 612 are situated between a cell working electrode 614 and a counter electrode 616, such that a voltage is applied across nanopore 602. Nanopore 602 is also in contact with a bulk liquid/electrolyte 618. Note that nanopore 602 and membrane 612 are drawn upside down as compared to the nanopore and membrane in FIG. 1. Hereinafter, a cell is meant to include at least a membrane, a nanopore, a working cell electrode, and the associated circuitry. In some embodiments, the counter electrode is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells. There is a working cell electrode within each measurement cell; in contrast to the common electrode, working cell electrode 614 is configurable to apply a distinct potential that is independent from the working cell electrodes in other measurement cells.

In FIGS. 7A and 7B, instead of showing a nanopore inserted in a membrane and the liquid surrounding the nanopore, an electrical model 702 representing the electrical properties of the nanopore and the membrane is shown. Electrical model 702 includes a capacitor 706 that models a capacitance associated with the membrane and a resistor 704 that models a resistance associated with the nanopore in different states (e.g., the open-channel state or the states corresponding to having different types of tag/molecule inside the nanopore). The respective circuitry in FIGS. 7A and 7B further includes an optional on-chip fabricated capacitor ($n_{cap}$ 714) that is in parallel to capacitor 706. In some embodiments, $n_{cap}$ 714 is added to fine tune the system, as will be described in greater detail below. In some embodiments, the extra on-chip capacitor is eliminated from the system to further reduce the size of the nanopore based sequencing chip.

Figure 8:
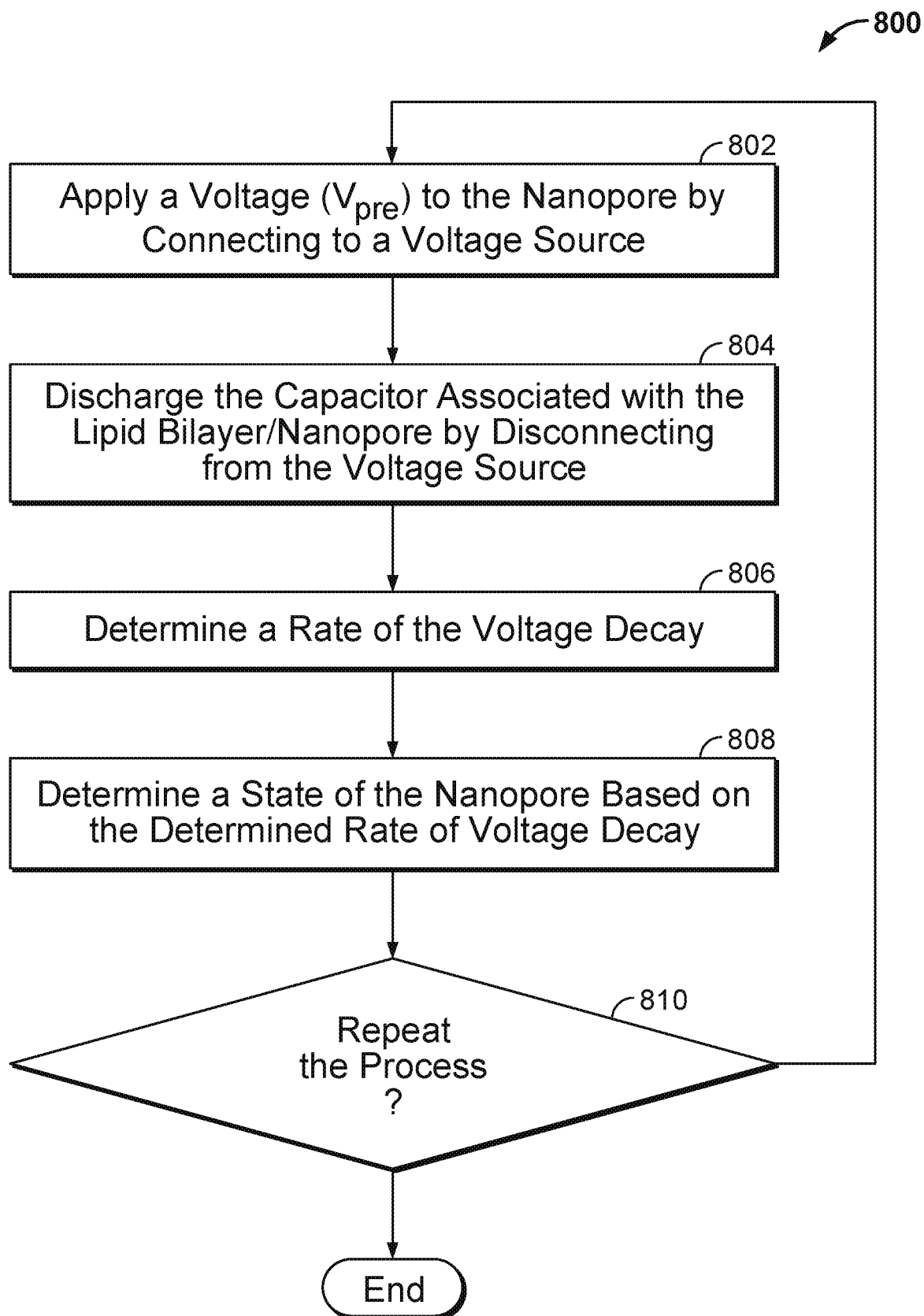
FIG. 8 illustrates an embodiment of a process 800 for analyzing a molecule inside a nanopore, wherein the nanopore is inserted in a membrane.
Figure 9:
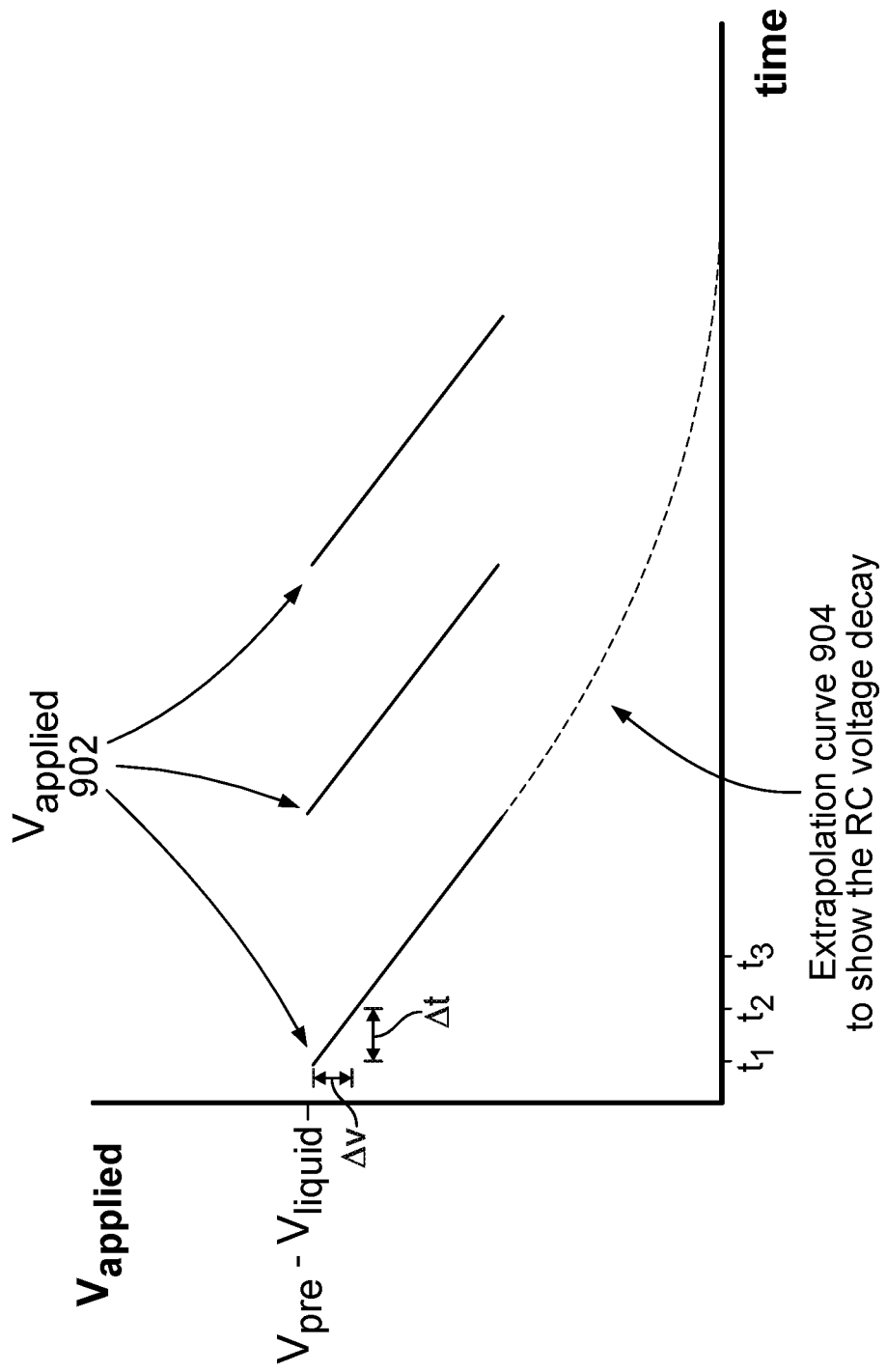
FIG. 9 illustrates an embodiment of a plot of the voltage applied across the nanopore versus time when process 800 is performed and repeated three times.

FIG. 8 illustrates an embodiment of a process 800 for analyzing a molecule inside a nanopore, wherein the nanopore is inserted in a membrane. Process 800 may be performed using the circuitries shown in FIG. 6, 7A, or 7B. FIG. 9 illustrates an embodiment of a plot of the voltage applied across the nanopore versus time when process 800 is performed and repeated three times. As will be described in greater detail below, the voltage applied across the nanopore is not held constant. Instead, the voltage applied across the nanopore changes over time. The rate of the voltage decay (i.e., the steepness of the slope of the applied voltage across the nanopore versus time plot) depends on the cell resistance (e.g., the resistance of resistor 704 in FIG. 7A). More particularly, as the resistance associated with the nanopore in different states (e.g., the open-channel state, the states corresponding to having different types of tag/molecule inside the nanopore, and the state when the membrane is ruptured) are different due to the molecules'/tags' distinct chemical structure, different corresponding rates of voltage decay may be observed and thus may be used to identify the different states of the nanopore.

With reference to FIG. 8 and FIG. 7A, at 802 of process 800, a voltage is applied across the nanopore by coupling the nanopore to a voltage source. For example, as shown in FIG. 7A, a voltage $V_{pre}$ 710 is applied to the cell working electrode when a switch S1 708 is closed. As shown in FIG. 9, the initial voltage applied across the nanopore is $V_{pre}$–$V_{liquid}$, where $V_{liquid}$ is the voltage of the bulk liquid in contact with the nanopore. As the voltage source is connected to the working electrode, the capacitor associated with the membrane is charged and energy is stored in an electric field across the membrane.

At 804 of process 800, the capacitor associated with the membrane (capacitor 706) is discharged by decoupling the nanopore and the membrane from the voltage source, and the energy stored in the electric field across the membrane is thereby dissipated. For example, as shown in FIG. 7A, the voltage source is disconnected when switch S1 708 is opened. After switch S1 708 is opened, the voltage across the nanopore begins to decay exponentially, as shown in FIG. 9. The exponential decay has a RC time constant τ=RC, where R is the resistance associated with the nanopore (resistor 704) and C is the capacitance in parallel with R, including the capacitance associated with the membrane C 706 and the capacitance associated with $n_{cap}$ 714.

At 806 of process 800, a rate of the decay of the voltage applied across the nanopore is determined. The rate of the voltage decay is the steepness of the slope of the applied voltage across the nanopore versus time curve, as shown in FIG. 9. The rate of the voltage decay may be determined in different ways.

In some embodiments, the rate of the voltage decay is determined by measuring the voltage decay that occurs during a fixed time interval. For example, as shown in FIG. 9, the voltage applied at the working electrode is first measured by ADC 712 at time $t_1$, and then the voltage is again measured by ADC 712 at time $t_2$. The voltage difference $\Delta V_{applied}$ is greater when the slope of the voltage across the nanopore versus time curve is steeper, and the voltage difference $\Delta V_{applied}$ is smaller when the slope of the voltage curve is less steep. Thus, $\Delta V_{applied}$ may be used as a metric for determining the rate of the decay of the voltage applied across the nanopore. In some embodiments, to increase the accuracy of the measurement of the rate of voltage decay, the voltage may be measured additional times at fixed intervals. For example, the voltage may be measured at $t_3$, $t_4$, and so on, and the multiple measurements of $\Delta V_{applied}$ during the multiple time intervals may be jointly used as a metric for determining the rate of the decay of the voltage applied across the nanopore. In some embodiments, correlated double sampling (CDS) may be used to increase the accuracy of the measurement of the rate of voltage decay.

In some embodiments, the rate of the voltage decay is determined by measuring the time duration that is required for a selected amount of voltage decay. In some embodiments, the time required for the voltage to drop from a fixed voltage $V_1$ to a second fixed voltage $V_2$ may be measured. The time required is less when the slope of the voltage curve is steeper, and the time required is greater when the slope of the voltage curve is less steep. Thus, the measured time required may be used as a metric for determining the rate of the decay of the voltage applied across the nanopore.

At 808 of process 800, a state of the nanopore is determined based on the determined rate of voltage decay. One of the possible states of the nanopore is an open-channel state during which a tag-attached polyphosphate is absent from the barrel of the nanopore. Other possible states of the nanopore correspond to the states when different types of molecules are held in the barrel of the nanopore. For example, another four possible states of the nanopore correspond to the states when the four different types of tag-attached polyphosphate (A, T, G, or C) are held in the barrel of the nanopore. Yet another possible state of the nanopore is when the membrane is ruptured. The state of the nanopore can be determined based on the determined rate of voltage decay, because the rate of the voltage decay depends on the cell resistance; i.e., the resistance of resistor 704 in FIG. 7A. More particularly, as the resistances associated with the nanopore in different states are different due to the molecules/tags' distinct chemical structure, different corresponding rates of voltage decay may be observed and thus may be used to identify the different states of the nanopore.

FIG. 10 illustrates an embodiment of the plots of the voltage applied across the nanopore versus time when the nanopore is in different states. Plot 1002 shows the rate of voltage decay during an open-channel state. In some embodiments, the resistance associated with the nanopore in an open-channel state is in the range of 100 Mohm to 20 Gohm. Plots 1004, 1006, 1008, and 1010 show the different rates of voltage decay corresponding to the four capture states when the four different types of tag-attached polyphosphate (A, T, G, or C) are held in the barrel of the nanopore. In some embodiments, the resistance associated with the nanopore in a capture state is within the range of 200 Mohm to 40 Gohm. Note that the slope of each of the plots is distinguishable from each other.

At 810 of process 800, it is determined whether process 800 is repeated. For example, the process may be repeated a plurality of times to detect each state of the nanopore. If the process is not repeated, then process 800 terminates; otherwise, the process restarts at 802 again. At 802, a voltage is reasserted across the nanopore by connecting the electrode to the voltage source. For example, as shown in FIG. 7A, a voltage $V_{pre}$ 710 is applied to the cell working electrode when switch S1 708 is closed. As shown in FIG. 9, the applied voltage jumps back up to the level of $V_{pre}-V_{liquid}$. As process 800 is repeated a plurality of times, a saw-tooth like voltage waveform is applied across the nanopore over time. FIG. 9 also illustrates an extrapolation curve 904 showing the RC voltage decay over time had the voltage $V_{pre}$ 710 not been reasserted.

As shown above, configuring the voltage applied across the nanopore to vary over a time period during which the nanopore is in a particular detectable state has many advantages. One of the advantages is that the elimination of the operational amplifier and the pass device that are otherwise fabricated on-chip in the cell circuitry significantly reduces the footprint of a single cell in the nanopore based sequencing chip, thereby facilitating the scaling of the nanopore based sequencing chip to include more and more cells (e.g., having millions of cells in a nanopore based sequencing chip). The capacitance in parallel with the nanopore includes two portions: the capacitance associated with the membrane and the capacitance associated with the integrated chip (IC). In some embodiments, due to the thin nature of the membrane, the capacitance associated with the membrane alone can suffice to create the required RC time constant without the need for additional on-chip capacitance, thereby allowing significant reduction in cell size and chip size.

Another advantage is that the circuitry of a cell does not suffer from offset inaccuracies because $V_{pre}$ is applied directly to the working electrode without any intervening circuitry. Another advantage is that since no switches are being opened or closed during the measurement intervals, the amount of charge injection is minimized.

Furthermore, the technique described above operates equally well using positive voltages or negative voltages. The voltage may be an alternating current (AC) voltage. Bidirectional measurements have been shown to be helpful in characterizing a molecular complex. In addition, bidirectional measurements are required when the type of ionic flow that is driven through the nanopore is via non-faradaic conduction. Two types of ionic flow can be driven through the nanopore: faradaic conduction and non-faradaic conduction. In faradaic conduction, a chemical reaction occurs at the surface of the metal electrode. The faradaic current is the current generated by the reduction or oxidation of some chemical substances at an electrode. The advantage of non-faradaic conduction is that no chemical reaction happens at the surface of the metal electrode.

Figure 11A:
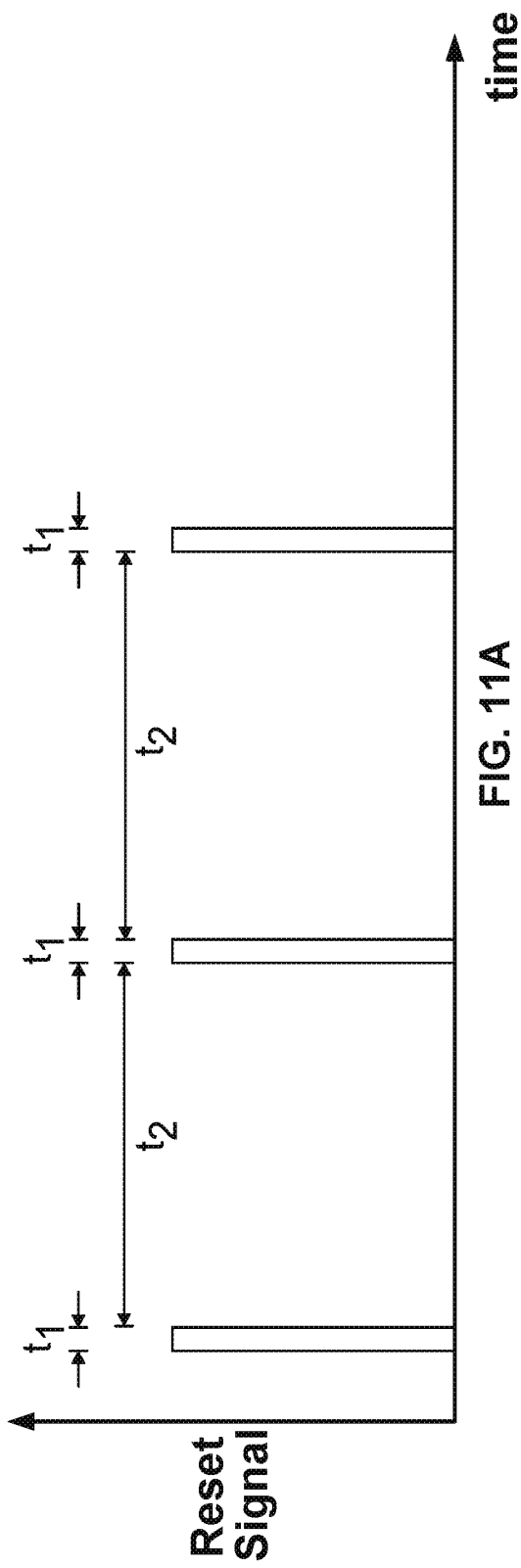
FIG. 11A illustrates an embodiment of a reset signal that is used to control the switch that connects or disconnects the voltage source to or from the membrane in a cell of the nanopore based sequencing chip, such that the capacitor associated with the membrane is charged and discharged repeatedly.
Figure 11B:
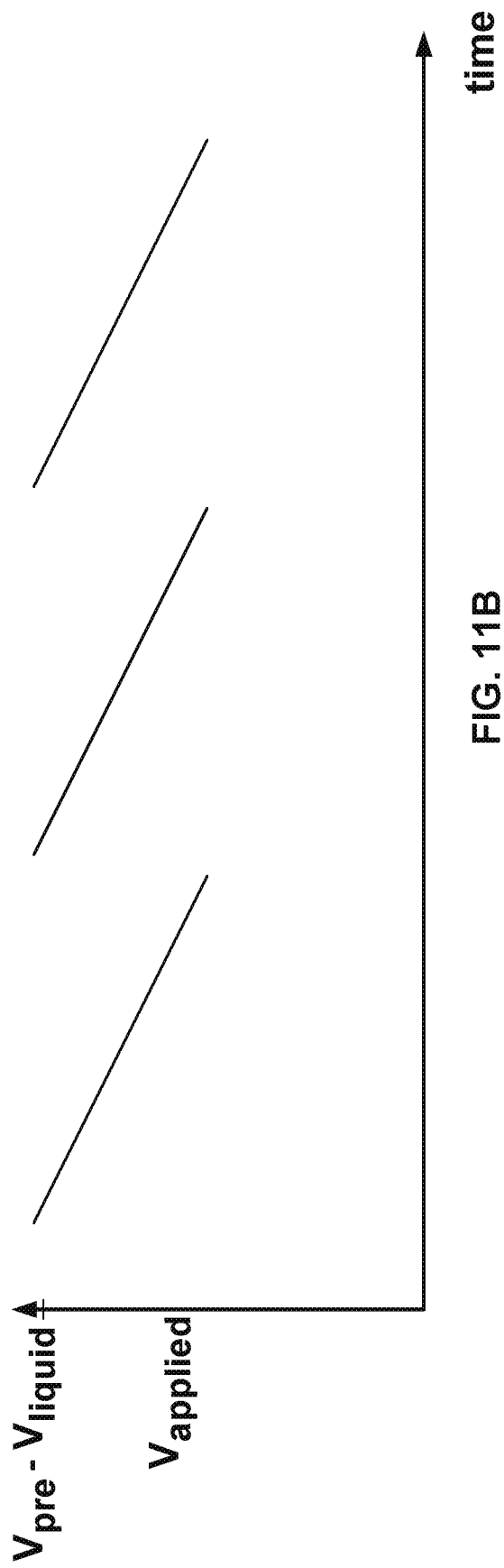
FIG. 11B illustrates the voltage applied across the nanopore in response to the reset signal in FIG. 11A as a function of time.

FIG. 11A illustrates an embodiment of a reset signal that is used to control the switch that disconnects or disconnects the voltage source to or from the membrane in a cell of the nanopore based sequencing chip, such that the capacitor associated with the membrane is charged and discharged repeatedly. FIG. 11B illustrates the voltage applied across the nanopore in response to the reset signal in FIG. 11A as a function of time.

When the reset signal is held at high during the time periods $t_1$, the switch is closed, and when the reset signal is held at low during the time periods $t_2$, the switch is open. For example, as shown in FIG. 7A, after switch S1 708 is closed, the voltage source is connected to the working electrode, applying a voltage $V_{pre}$ 710 to the cell working electrode, and the capacitor associated with the membrane (C 706) and $n_{cap}$ 714 are charged to the voltage $V_{pre}$. As shown in FIG. 11B, when the capacitors are fully charged, the voltage applied across the nanopore is $V_{pre}-V_{liquid}$, where $V_{liquid}$ is the voltage of the bulk liquid in contact with the nanopore. Immediately after the capacitors are charged, switch S1 708 is opened by the low reset signal during time period $t_2$, decoupling the nanopore and the membrane from the voltage source, and the energy stored in the electric field across the membrane is thereby dissipated. During this integrating time $t_2$, the capacitors are discharged, and the voltage across the nanopore begins to decay exponentially, as shown in FIG. 11B. The exponential decay has a RC time constant $\tau=RC$, where R is the resistance associated with the nanopore (resistor 704) and C is the capacitance in parallel with R, including the capacitance associated with the membrane C 706 and the capacitance associated with $n_{cap}$ 714.

In the embodiment shown in FIGS. 11A and 11B, the reset signal is kept high for a very brief period only and as soon as the capacitors are charged, the capacitors are discharged and the rate of decay is determined. This results in the saw tooth voltage decay pattern as shown in FIG. 11B. The voltage applied across the nanopore is at a maximum during a short time period $t_1$, but continues to decrease throughout a longer time period $t_2$. Since the tag is pulled into the nanopore by the electrical force generated by the voltage applied across the membrane, lower voltage levels applied across the nanopore during the integration time period $t_2$ may cause a tag that is already trapped in the nanopore to escape from the nanopore. In addition, if a tag is within a close proximity to the nanopore and is poised to be pulled into the nanopore, a continuously decreasing applied voltage reduces the chance that the tag is captured into the nanopore. Therefore, the voltage applied across the nanopore over time may affect the performance of the nanopore based sequencing chip, and an improved applied voltage pattern across the nanopore would be desirable.

Figure 12A:
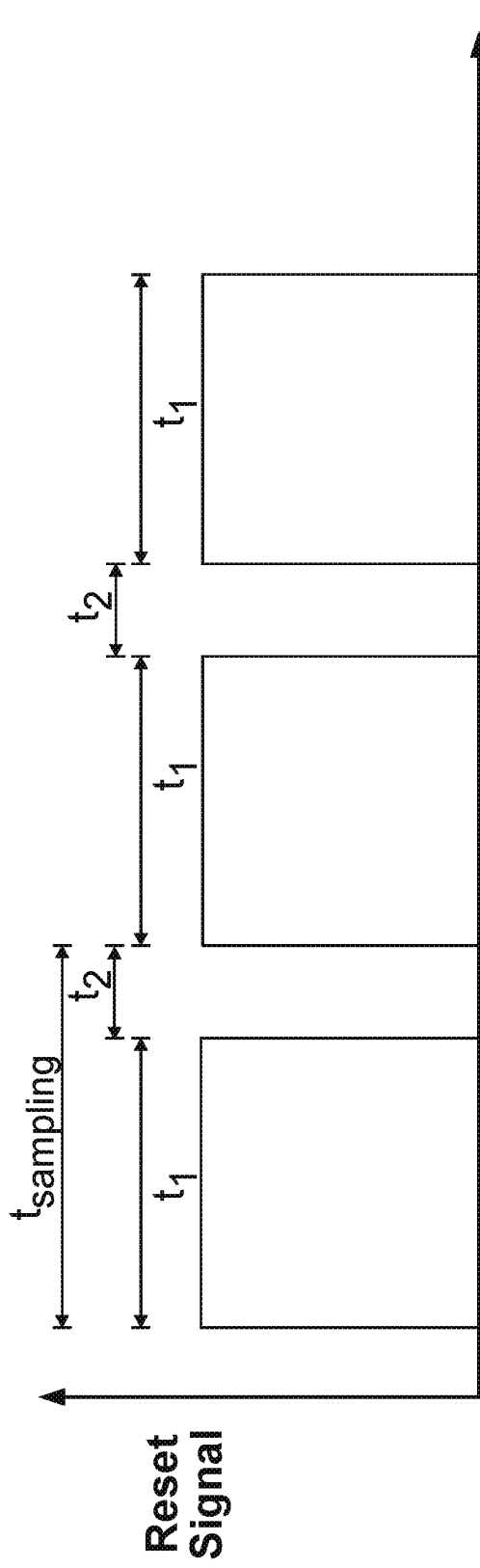
FIG. 12A illustrates another embodiment of a reset signal that is used to control the switch that connects or disconnects the voltage source to or from the membrane in a cell of the nanopore based sequencing chip, such that the capacitance associated with the membrane is charged and discharged repeatedly.
Figure 12B:
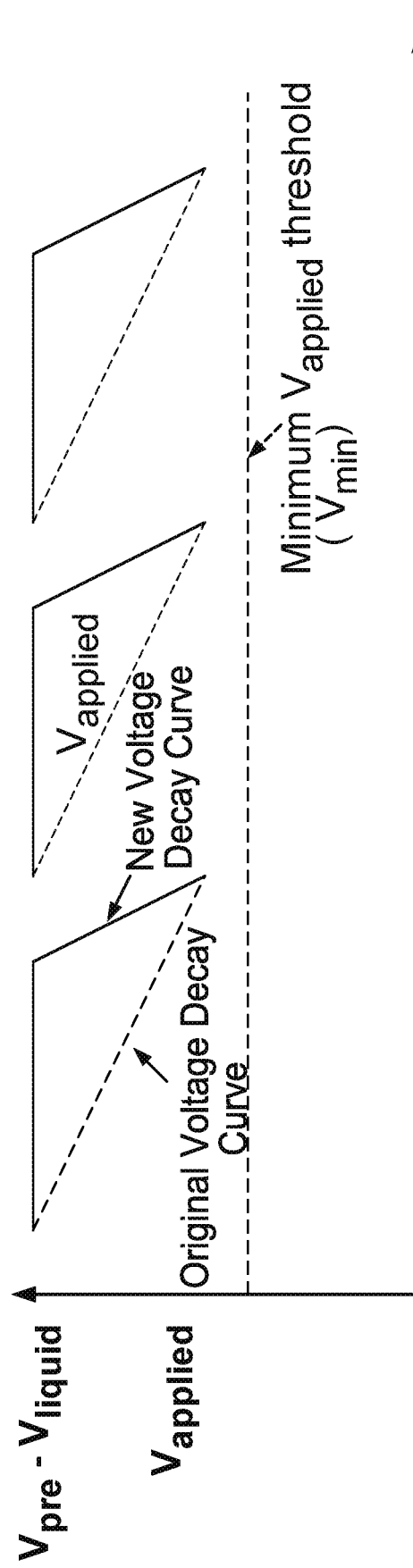
FIG. 12B illustrates the voltage applied across the nanopore in response to the reset signal in FIG. 12A as a function of time.

FIG. 12A illustrates another embodiment of a reset signal that is used to control the switch that connects or disconnects the voltage source to or from the membrane in a cell of the nanopore based sequencing chip, such that the capacitor associated with the membrane is charged and discharged repeatedly. FIG. 12B illustrates the voltage applied across the nanopore in response to the reset signal in FIG. 12A as a function of time.

When the reset signal is held at high during the time periods $t_1$, the switch is closed, and when the reset signal is held at low during the time periods $t_2$, the switch is open. For example, as shown in FIG. 7A, after switch S1 708 is closed, the voltage source is connected to the working electrode, applying a voltage $V_{pre}$ 710 to the cell working electrode, and the capacitor associated with the membrane (C 706) and $n_{cap}$ 714 are charged to the voltage $V_{pre}$. As shown in FIG. 12B, when the capacitors are fully charged, the voltage applied across the nanopore is $V_{pre}-V_{liquid}$, where $V_{liquid}$ is the voltage of the bulk liquid in contact with the nanopore. After the capacitors are fully charged, switch S1 708 is kept closed by the high reset signal during time period $t_1$, thereby maintaining the voltage applied across the nanopore at $V_{pre}-V_{liquid}$ during time period $t_1$. Switch S1 708 is then opened by the low reset signal during time period $t_2$, decoupling the nanopore and the membrane from the voltage source, and the energy stored in the electric field across the membrane is thereby dissipated. During this shortened integrating time $t_2$, the capacitors are discharged, and the voltage across the nanopore decays exponentially, as shown in FIG. 12B. The exponential decay has a RC time constant $\tau=RC$, where R is the resistance associated with the nanopore (resistor 704) and C is the capacitance in parallel with R, including the capacitance associated with the membrane C 706 and the capacitance associated with $n_{cap}$ 714.

In the embodiment shown in FIGS. 12A and 12B, the reset signal is kept high after the capacitors are fully charged. The duty cycle of the reset signal is the percentage of one reset signal period during which the reset signal is ON, wherein one reset signal period is the time it takes the reset signal to complete an ON-and-OFF cycle. The duty cycle of the reset signal in FIG. 12A is $t_1/(t_1+t_2)$. As shown in FIG. 12A, one period of the reset signal is also the sampling period, $t_{sampling}$, in which the measurement data corresponding to a single voltage decay curve of a cell is sampled and outputted from the chip. The sampling frequency is $1/t_{sampling}$. The duty cycle of the reset signal is also the percentage of one sampling period during which the voltage applied across the nanopore is held at a high level. As an illustrative example, one particular embodiment has a sampling rate of 1 kHz and a sampling period of 1 ms, and the duty cycle is 0.8, with $t_1=800$ μs and $t_2=200$ μs. The duty cycle is at least 0.1. However, the duty cycle may be different in different embodiments and may be adjusted for optimized performance based on different factors and constraints of the system, as will be described in greater detail below.

By increasing the duty cycle of the reset signal, the voltage applied across the nanopore is held constant at a high level for a portion of the sampling period $t_{sampling}$, the exponential decay is delayed to a latter portion of the sampling period, and the duration of the voltage exponential decay is shortened as compared to the original exponential voltage decay in FIG. 11B (also shown as a dashed curve in FIG. 12B). The average voltage applied across the nanopore during the sampling period is also increased. As a result, a tag that is already trapped in the nanopore is less likely to escape from the nanopore due to a lower applied voltage across the nanopore. In addition, a tag that is within a close proximity to the nanopore has a higher chance of being pulled into the nanopore by the electrical force generated by the voltage applied across the membrane. The probabilities that the tags get captured and stay captured in a nanopore are both increased. Having a steady applied voltage over a significant portion of a sampling period, as opposed to having a varying voltage throughout the entire sampling period, also provides a more stable environment for the chemicals of the cell to operate within. In addition, the integration time is no longer tied to the sampling period. Decoupling the integration time from the sampling period is advantageous because the integration time can be reduced without increasing the sampling frequency, which may otherwise cause a significant increase in output data.

The duty cycle of the reset signal may be adjusted for optimized performance based on different factors and constraints of the system or user inputs, for example by a processor. One of the constraints in determining the duty cycle is the minimum voltage applied across the nanopore. The predetermined minimum voltage applied across the nanopore should be high enough such that the tags can be captured and stay captured in the nanopore. In some embodiments, the minimum voltage is 60% of the initial voltage. For example, if the initial voltage before any discharge is 100 mV, then the minimum voltage may be maintained above 60 mV.

As shown in FIG. 12B, although the new voltage decay curve may use a different RC time constant and thus have a steeper slope and faster decay than the original voltage decay curve, the lowest voltage applied across the nanopore may be maintained above the same predetermined minimum $V_{applied}$ threshold, $V_{min}$, and the corresponding duty cycle may be determined based on the relationships as shown below.

The exponential decay has a RC time constant $\tau=RC$, where R is the resistance associated with the nanopore (resistor 704) and C is the capacitance in parallel with R, including the capacitance associated with the membrane C 706 and the capacitance associated with $n_{cap}$ 714. One way to achieve a faster voltage decay is to decrease the capacitance in parallel with R. In some embodiments, the capacitance of $n_{cap}$ 714 is about 40 fF and the capacitance associated with the membrane C 706 is about 25 fF. However, other combinations of capacitances may be used as well. The voltage decay is described by the following relationship:

$$V(t)=V_0(e^{-t/\tau})\qquad\text{Equation 1}$$

where V(t) is the voltage of the capacitors at time t after the switch 708 opens, $V_0$ is the voltage of the capacitors prior to any discharge ($V_{pre}$), and τ is the RC time constant.

Therefore, given a predetermined minimum $V_{applied}$ threshold, $V_{min}$, and a given $t_{sampling}$, $t_2$ may be determined using Equation 2 below:

$$V_{min}=V_{pre}(e^{-t2/\tau})-V_{liquid}\qquad\text{Equation 2}$$

and the duty cycle may be determined using Equation 3 below:

$$\text{duty cycle}=(t_{sampling}-t_2)/t_{sampling}\qquad\text{Equation 3}$$

Another constraint in determining the duty cycle is the amount of decay of $V_{applied}$ during the integrating period $t_2$. The absolute or relative drop in $V_{applied}$ should be large enough in order to maintain a satisfactory signal-to-noise ratio at the ADC (e.g., ADC converter 510). The threshold amount of reduction in $V_{applied}$ may be maintained by adjusting the duty cycle, which can be determined based on Equations 1-3 described above.

In some embodiments, the duty cycle may be optimized such that the time period $t_1$ during which $V_{applied}$ is held steady is maximized, while keeping the absolute or relative voltage decay and/or the minimum $V_{applied}$ across the nanopore above certain predetermined respective thresholds.

In some embodiments, the duty cycle of the reset signal may be dynamically adjusted such that different types of salt solution/electrolyte and different concentrations of the salt solution/electrolyte may be used by the nanopore based sequencing chip. The steepness of the voltage decay curve is affected by the different types of salt solution/electrolyte and different concentrations of the salt solution/electrolyte used. In order to provide the flexibility of selecting different types of salt and the salt concentration level to the end-user of the chip, the chip may receive user indications of the type of salt and concentration of the salt solution as inputs, and the duty cycle may be dynamically adjusted for optimized performance. In some embodiments, the salt concentration is 500 mM, and $t_1$=870 µs, $t_2$=130 µs, and the duty cycle=0.87. In some embodiments, the salt concentration is 250 mM, and $t_1$=740 µs, $t_2$=260 µs, and the duty cycle=0.74.

Figure 13:
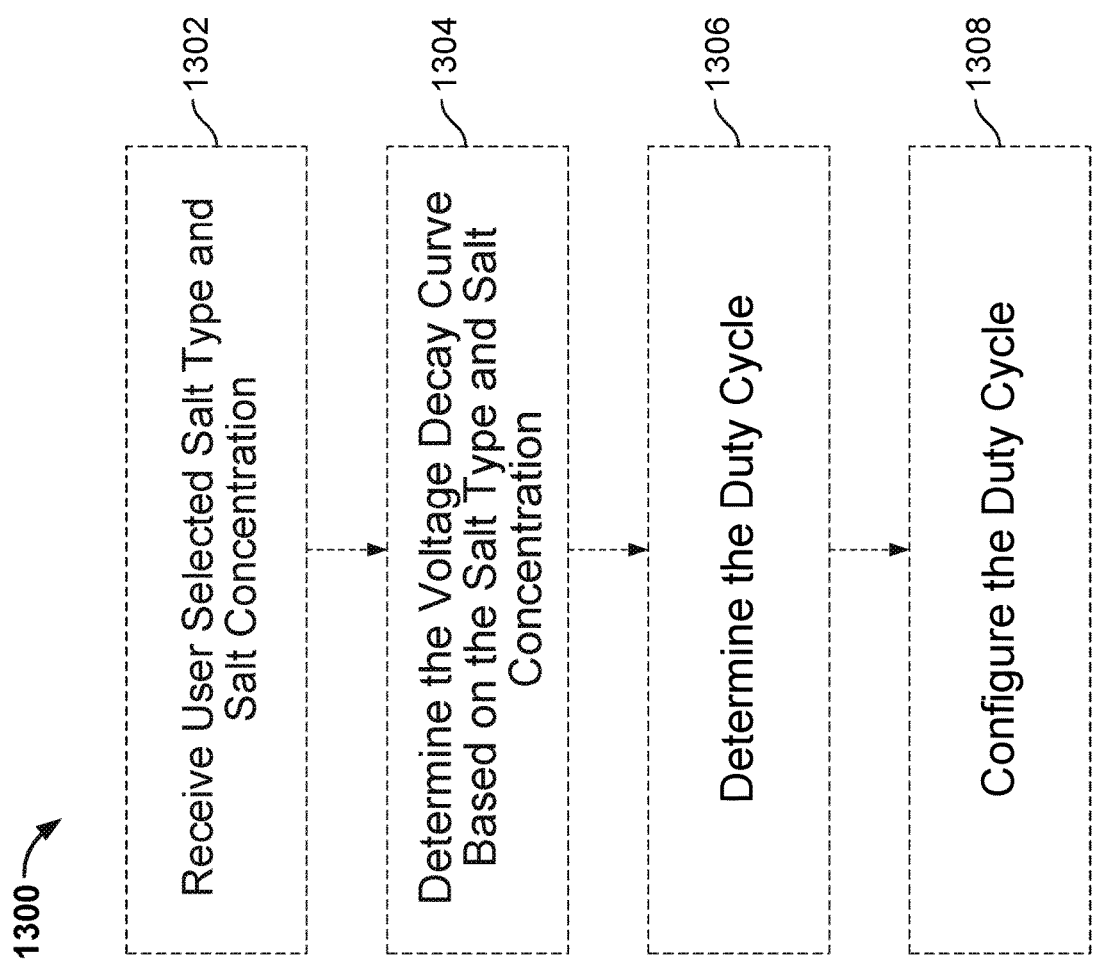
FIG. 13 illustrates an embodiment of a process 1300 for dynamically configuring the duty cycle of the reset signal based on the salt type and salt concentration.

FIG. 13 illustrates an embodiment of a process 1300 for dynamically configuring the duty cycle of the reset signal based on the salt type and salt concentration. At 1302, user indications of the type of salt and concentration of the salt solution are received as inputs. At 1304, characteristics of the voltage decay curve (e.g., the slope) are determined based on the type of salt and concentration of the salt solution. At 1306, the duty cycle of the reset signal is optimized such that the time period $t_1$ during which $V_{applied}$ is held steady is maximized, while keeping the absolute or relative voltage decay and/or the minimum $V_{applied}$ across the nanopore above certain predetermined respective thresholds. At 1308, the duty cycle of the reset signal is configured.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for analyzing a molecule in a nanopore, the system comprising:
   a voltage source;
   a capacitor;
   a working electrode in electrical communication with the capacitor;
   a counter electrode;
   a switch configured to selectively connect the voltage source with the capacitor or disconnect the voltage source from the capacitor, wherein the capacitor is configured to store a charge received from the voltage source when the voltage source is connected to the capacitor and wherein the capacitor is configured to discharge the stored charge through a nanopore in a membrane disposed between the working electrode and the counter electrode when the voltage source is disconnected from the capacitor; and
   a processor programmed to:
      determine a rate of voltage decay across the capacitor when the voltage source is disconnected from the capacitor; and
      determine the state of the nanopore based on the determined rate of voltage decay, wherein the state of the nanopore is selected from the group consisting of an open channel, a first molecule disposed within the nanopore, a second molecule disposed within the nanopore, a third molecule disposed within the nanopore, and a fourth molecule disposed within the nanopore.

2. The system of claim 1, wherein the switch is configured to selectively connect the voltage source with the capacitor or disconnect the voltage source form the capacitor with a reset signal.

3. The system of claim 2, wherein the reset signal has a duty cycle that turns on the switch to connect the voltage source and turns off the switch to disconnect the voltage source such that the voltage between the working electrode and the counter electrode drops less than 40% during the discharge portion of the duty cycle.

4. The system of claim 2, wherein the reset signal has a duty cycle that is configured so that the switch is turned on for at least 10% of each cycle.

5. The system of claim 1, wherein the first molecule, second molecule, third molecule, and fourth molecule correspond to different types of nucleotides.

6. A system for analyzing a molecule in a nanopore, the system comprising:
   a voltage source;
   a capacitor;
   a working electrode in electrical communication with the capacitor;
   a counter electrode;
   a switch configured to selectively connect the voltage source with the capacitor or disconnect the voltage source from the capacitor, wherein the capacitor is configured to store a charge received from the voltage source when the voltage source is connected to the capacitor and wherein the capacitor is configured to discharge the stored charge through a nanopore in a membrane disposed between the working electrode and the counter electrode when the voltage source is disconnected from the capacitor, wherein the switch is configured to selectively connect both the capacitor and the working electrode with the voltage source or to disconnect both the capacitor and the working electrode from the voltage source; and a processor programmed to:
  determine a rate of voltage decay across the capacitor when the voltage source is disconnected from the capacitor; and
  determine the state of the nanopore based on the determined rate of voltage decay.

7. A system for analyzing a molecule in a nanopore, the system comprising:
  a voltage source;
  a capacitor;
  a working electrode in electrical communication with the capacitor;
  a counter electrode;
  a switch configured to selectively connect the voltage source with the capacitor or disconnect the voltage source from the capacitor, wherein the capacitor is configured to store a charge received from the voltage source when the voltage source is connected to the capacitor and wherein the capacitor is configured to discharge the stored charge through a nanopore in a membrane disposed between the working electrode and the counter electrode when the voltage source is disconnected from the capacitor; and
  a processor programmed to:
    determine a rate of voltage decay across the capacitor when the voltage source is disconnected from the capacitor; and
    determine the state of the nanopore based on the determined rate of voltage decay, wherein the rate of voltage decay is determined by measuring a magnitude of a drop in voltage over a fixed time interval.

8. A system for analyzing a molecule in a nanopore, the system comprising:
  a voltage source;
  a capacitor;
  a working electrode in electrical communication with the capacitor;
  a counter electrode;
  a switch configured to selectively connect the voltage source with the capacitor or disconnect the voltage source from the capacitor, wherein the capacitor is configured to store a charge received from the voltage source when the voltage source is connected to the capacitor and wherein the capacitor is configured to discharge the stored charge through a nanopore in a membrane disposed between the working electrode and the counter electrode when the voltage source is disconnected from the capacitor; and
  a processor programmed to:
    determine a rate of voltage decay across the capacitor when the voltage source is disconnected from the capacitor; and
    determine the state of the nanopore based on the determined rate of voltage decay, wherein the rate of voltage decay is determined by measuring a length of time required for a fixed voltage drop.

9. A system for analyzing a molecule in a nanopore, the system comprising:
  a voltage source;
  a capacitor;
  a working electrode in electrical communication with the capacitor;
  a counter electrode;
  a switch configured to selectively connect the voltage source with the capacitor or disconnect the voltage source from the capacitor, wherein the capacitor is configured to store a charge received from the voltage source when the voltage source is connected to the capacitor and wherein the capacitor is configured to discharge the stored charge through a nanopore in a membrane disposed between the working electrode and the counter electrode when the voltage source is disconnected from the capacitor; and
  a processor programmed to:
    determine a magnitude of a drop in voltage across the capacitor over a fixed time interval when the voltage source is disconnected from the capacitor; and
    determine the state of the nanopore based on the determined magnitude of the drop in voltage, wherein the state of the nanopore is selected from the group consisting of an open channel, a first molecule disposed within the nanopore, a second molecule disposed within the nanopore, a third molecule disposed within the nanopore, and a fourth molecule disposed within the nanopore.

10. The system of claim 9, wherein the first molecule, second molecule, third molecule, and fourth molecule correspond to different types of nucleotides.

11. A system for analyzing a molecule in a nanopore, the system comprising:
  a voltage source;
  a capacitor;
  a working electrode in electrical communication with the capacitor;
  a counter electrode;
  a switch configured to selectively connect the voltage source with the capacitor or disconnect the voltage source from the capacitor, wherein the capacitor is configured to store a charge received from the voltage source when the voltage source is connected to the capacitor and wherein the capacitor is configured to discharge the stored charge through a nanopore in a membrane disposed between the working electrode and the counter electrode when the voltage source is disconnected from the capacitor; and
  a processor programmed to:
    determine a length of time required for a fixed drop in voltage across the capacitor when the voltage source is disconnected from the capacitor; and
    determine the state of the nanopore based on the determined length of time.

12. The system of claim 11, wherein the state of the nanopore is selected from the group consisting of an open channel, a first molecule disposed within the nanopore, a second molecule disposed within the nanopore, a third molecule disposed within the nanopore, and a fourth molecule disposed within the nanopore.

13. The system of claim 12, wherein the first molecule, second molecule, third molecule, and fourth molecule correspond to different types of nucleotides.

* * * * *